(12) United States Patent
He et al.

(10) Patent No.: US 12,171,616 B2
(45) Date of Patent: Dec. 24, 2024

(54) BRILLOUIN-OPTICAL COHERENCE-SPECKLE BASED MULTI-MODE ELASTICITY MEASUREMENT DEVICE

(71) Applicant: Nanchang Hangkong University, Nanchang (CN)

(72) Inventors: Xingdao He, Nanchang (CN); Jiulin Shi, Nanchang (CN); Yubao Zhang, Nanchang (CN); Zhongqi Hao, Nanchang (CN); Gang Shi, Nanchang (CN); Jin Xu, Nanchang (CN)

(73) Assignee: Nanchang Hangkong University, Nanchang (CN)

( * ) Notice: Subject to any disclaimer, the term of this patent is extended or adjusted under 35 U.S.C. 154(b) by 164 days.

(21) Appl. No.: 18/095,924

(22) Filed: Jan. 11, 2023

(65) Prior Publication Data

US 2024/0032895 A1    Feb. 1, 2024

(30) Foreign Application Priority Data

Jul. 28, 2022  (CN) .......................... 202210895119.4

(51) Int. Cl.
*A61B 8/08*    (2006.01)
*A61B 5/00*    (2006.01)
*A61B 8/00*    (2006.01)

(52) U.S. Cl.
CPC ............ *A61B 8/485* (2013.01); *A61B 5/0066* (2013.01); *A61B 8/4416* (2013.01); *A61B 2562/0233* (2013.01)

(58) Field of Classification Search
CPC ...... A61B 8/485; A61B 8/4416; A61B 5/0066
See application file for complete search history.

(56) References Cited

U.S. PATENT DOCUMENTS

2016/0206194 A1* 7/2016 Vogler .................. A61B 3/107

* cited by examiner

*Primary Examiner* — Gerald Johnson
(74) *Attorney, Agent, or Firm* — Kunzler Bean & Adamson; Michael Bartholomew

(57) ABSTRACT

Disclosed is a Brillouin-optical coherence-speckle based multi-mode elasticity measurement device, including a Brillouin-optical coherence elastography common-path scanning unit, a Brillouin scattering elastography system, an optical coherence elastography system, a speckle elastography system, and a time sequence controller, where the Brillouin scattering elastography system and the optical coherence elastography system share the Brillouin-optical coherence elastography common-path scanning unit. According to the present invention, advantages that Brillouin scattering elastography can perform high-precision measurement on a bulk elasticity modulus, optical coherence elastography can rapidly obtain an elasticity distribution of an entire sample to perform three-dimensional elasticity mapping, and laser speckle elastography can perform wide-field elasticity measurement are utilized to perform in-situ synchronous imaging on elasticity distribution of lesion tissue, so that scientific basis and technical support are provided for early diagnosis of clinical diseases.

8 Claims, 1 Drawing Sheet

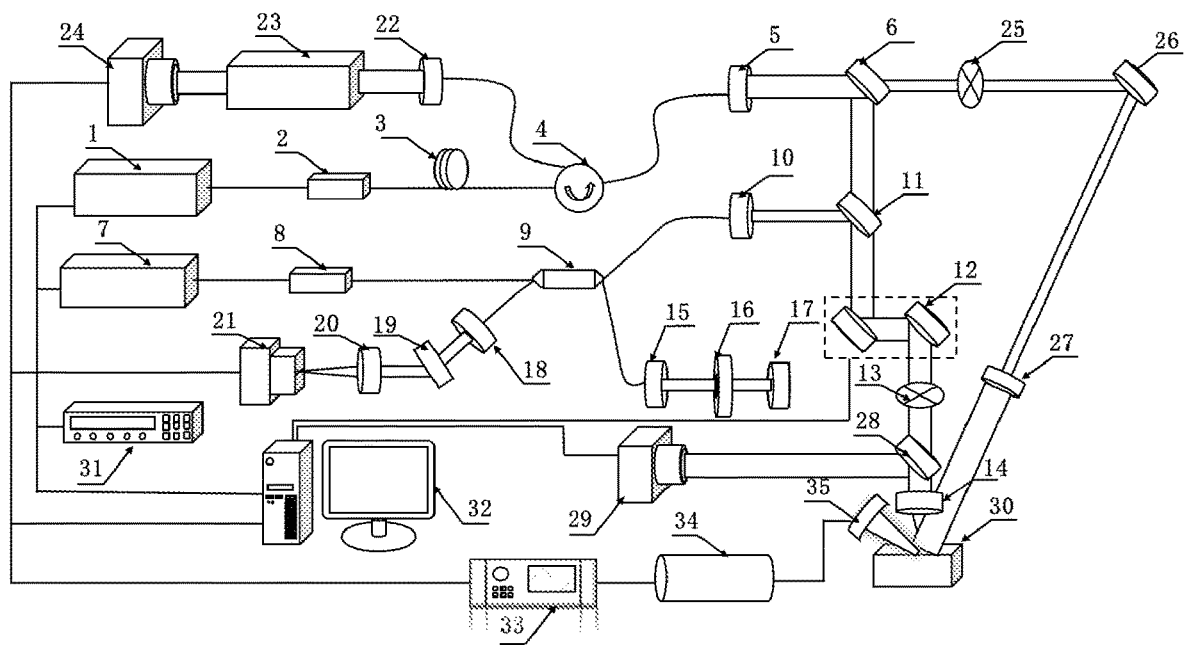

BRILLOUIN-OPTICAL COHERENCE-SPECKLE BASED MULTI-MODE ELASTICITY MEASUREMENT DEVICE

REFERENCE TO PRIOR APPLICATION

This application claims priority to Chinese Patent Application 202210895119.4, filed on 28 Jul. 2022.

TECHNICAL FIELD

The present invention relates to the technical field of imaging devices, and in particular to a Brillouin-optical coherence-speckle based multi-mode elasticity measurement device.

DESCRIPTION OF RELATED ART

As an elasticity measurement device, the present invention is principally configured to detect the elasticity distribution of the biological tissue by combining Brillouin scattering elastography (BSE), optical coherence elastography (OCE), and laser speckle elastography (LSE). The inventive concept lies in that for the lesion tissue such as malignant tumors, brain injuries, skin cancers, etc., the development of the disease cannot be fully determined through the structural images in the early stage of the disease. The biomechanical characteristics of the tissue are of great significance in evaluating tissue function and state, and thus provide unique information for clinical disease prevention, diagnosis, and monitoring. Owing to structure and interaction changes at the molecular, cellular, and tissue levels, the differences in biomechanical characteristic have been evaluated in the traditional clinical practice. For example, as a classic method for evaluating changes in biomechanical characteristic, palpation has been used to detect breast cancers, to evaluate abdominal organ functions, and to diagnose skin diseases in a wide range. However, palpation can only qualitatively evaluate the disease progression on the basis of tissue stiffness, relying on personal experience and lacking clinical criteria. Therefore, the study on a novel technology to obtain the elasticity information of the biological tissue has the great application value and significant for human health and disease diagnosis.

In the elastography, Brillouin scattering is an inelastic scattering process, having the spectral characteristics closely related to the properties of the medium (such as the density, viscosity, elasticity modulus, etc.). Therefore, the Brillouin scattering elastography (BSE) can be employed to measure the bulk elasticity modulus of the biological tissue by calculating the Brillouin frequency shift. As a novel elasticity measurement method based on optical coherence tomography, the optical coherence elastography (OCE) quantifies the elasticity moduli (such as the shear modulus and the Young's modulus) of the biological tissue by detecting the propagation information of elastic waves in the biological tissue, thereby realizing high-resolution and non-invasive evaluation of the biomechanical properties of the biological tissue. In the laser speckle elastography (LSE), scattered particles on the surface of the tissue will backscatter the incident light. Owing to the different optical path differences between different scattered lights to the imaging plane of the camera, different scattered lights will form the random interference phenomenon on the image plane, and shows as a particle pattern having brightness changes on spatial distribution. During imaging, the sample is vibrated through an external excitation device, and the propagation of the Rayleigh wave is tracked through the speckle contrast imaging system to calculate the elasticity coefficient and the viscosity coefficient of the measured sample.

Therefore, the BSE-OCE-LSE multi-mode elastography system device can synchronously measure the biomechanical characteristics of the lesion tissue in situ, thereby providing the scientific basis for disease prevention and diagnosis.

SUMMARY

An objective of the present invention is to provide a multi-mode imaging system for measuring elasticity, to solve the technical problems in the prior art.

In order to realize the objective described above, a technical solution provided by the present invention is as follows: a Brillouin-optical coherence-speckle based multi-mode elasticity measurement device includes a Brillouin-optical coherence elastography common-path scanning unit, a Brillouin scattering elastography system, an optical coherence elastography system, a speckle elastography system, and a time sequence controller, where the Brillouin scattering elastography system and the optical coherence elastography system share the Brillouin-optical coherence elastography common-path scanning unit, and the Brillouin-optical coherence elastography common-path scanning unit is composed of a dichroic mirror, a scanning galvanometer, a first optical shutter, and an objective lens; where the Brillouin scattering elastography system includes a Brillouin signal excitation unit and a Brillouin signal acquisition unit, the Brillouin signal excitation unit being configured to excite a Brillouin scattering signal, and the Brillouin signal acquisition unit being configured to acquire a Brillouin spectrum signal, so as to calculate a bulk elasticity modulus; the optical coherence elastography system includes an optical coherence tomography unit and an acoustic radiation force excitation unit, the optical coherence tomography unit being configured to collect an interference signal generated in a sample, and the acoustic radiation force excitation unit being configured to generate vibration for the sample, so as to generate wave propagation; the speckle elastography system includes a speckle signal excitation unit and a speckle signal acquisition unit, the speckle signal excitation unit being configured to excite a wide-view field speckle signal generated on a surface of the sample, and the speckle signal acquisition unit being configured to collect the wide-view field speckle signal generated on the surface of the sample, so as to generate elasticity information; and the time sequence controller is principally configured for step running of the Brillouin scattering elastography system, the optical coherence elastography system, and the speckle elastography system.

Preferably, the Brillouin scattering signal excitation unit is composed of a narrow linewidth continuous laser, a first optical fiber isolator, an optical fiber delay line, an optical fiber circulator, a first collimator, and a beam splitter; the Brillouin signal acquisition unit is composed of a fifth collimator, a Brillouin spectrometer, and a first detector; and in the Brillouin elastography system, the narrow linewidth continuous laser emits a light beam, the light beam passes through the first optical fiber isolator, the optical fiber delay line, port 1 of the optical fiber circulator, port 2 of the optical fiber circulator, and the first collimator, and is then split by the beam splitter, a reflected light passes through the dichroic mirror, a galvanometer set, and the first optical shutter, is then focused on a surface of the sample by the objective lens, and interacts with the sample to generate backward Brillouin scattering, a backward Brillouin scattered light of the sample returns along an original optical path, is output from port 3 of the optical fiber circulator, and collimated by the fifth collimator, enters the Brillouin spectrometer for frequency discrimination, and is finally received by the first detector.

Preferably, the Brillouin scattering elastography system, the optical coherence elastography system, and the speckle elastography system are integrated, and light beams emitted by the laser reach the sample at the same time for measurement through the time sequence controller and the optical fiber delay line, so that in-situ synchronous measurement on elasticity of the sample in a wide-view field, high-speed, and high-precision manner is realized.

Preferably, the optical coherence tomography unit is composed of an ultra-wideband light emitting diode, a second optical fiber isolator, a 2*2 optical fiber coupler, a second collimator, a reference arm, a grating spectrometer, and a linear array charge coupled device (CCD) 21; the acoustic radiation force excitation unit is composed of a signal generator, a power amplifier, and an ultrasonic transducer; in the optical coherence elastography system, the ultra-wideband light emitting diode emits a light beam, the light beam is collimated by the second optical fiber isolator, the 2*2 optical fiber coupler, and the second collimator, and then reflected by the dichroic mirror, a reflected light passes through a galvanometer set and the first optical shutter, and is then focused on the sample to be detected by the objective lens, a backscattered light generated through an interaction with the sample returns along an original path, interferes with a light beam returned by the reference arm in the 2*2 optical fiber coupler, enters the grating spectrometer, and is acquired and received by the linear array CCD; and moreover, a trigger signal generated by the optical coherence elastography system is synchronized with the signal generator to generate a sine wave signal which is amplified by the power amplifier to excite the sample through the ultrasonic transducer, so that the sample vibrates, and is acquired by the optical coherence tomography unit in the optical coherence elastography system.

Preferably, the ultrasonic transducer includes an ultrasonic generation unit and an impedance matching couplant, the impedance matching couplant being principally attached to the ultrasonic generation unit for matching a third medium so as to reduce attenuation of acoustic radiation power in the case of propagation in air.

Preferably, the speckle signal excitation unit is composed of a narrow linewidth continuous laser, a first optical fiber isolator, an optical fiber delay line, an optical fiber circulator, a first collimator, a beam splitter, a second optical shutter, a second plane reflector, and a beam expander; the speckle signal acquisition unit is composed of an objective lens, a turnover reflector, and a second detector; and in a speckle detection system, the narrow linewidth continuous laser emits a light beam, the light beam passes through the first optical fiber isolator, the optical fiber delay line, port 1 of the optical fiber circulator, port 2 of the optical fiber circulator, and the first collimator, and is then split by the beam splitter, a light beam transmitted through the beam splitter passes through the second optical shutter, the second plane reflector, and the beam expander, and is then incident on the sample to be detected, and a scattered signal generated through an interaction with the sample to be detected is reflected by the turnover reflector into the second detector through the objective lens for detection.

Preferably, the speckle signal excitation unit and the Brillouin-optical coherence elastography common-path scanning unit are alternately used by alternately using the first optical shutter, the second optical shutter, and the turnover reflector.

Preferably, the Brillouin-optical coherence elastography common-path scanning unit scans a surface X-Y of the sample through a galvanometer set to obtain a three-dimensional elasticity distribution of optical coherence elastography (OCE), and the sample at different depths by adjusting a focal length of the objective lens to obtain a three-dimensional Brillouin elasticity distribution image.

The present invention has the beneficial effects as follows:

According to the present invention, advantages that Brillouin scattering elastography may perform high-precision measurement on a bulk elasticity modulus, optical coherence elastography may rapidly obtain an elasticity distribution of an entire sample to perform three-dimensional elasticity mapping, and laser speckle elastography may perform wide-field elasticity measurement are utilized to perform in-situ synchronous imaging on an elasticity distribution of lesion tissue, so that scientific basis and technical support are provided for early diagnosis of clinical diseases.

BRIEF DESCRIPTION OF THE DRAWINGS

The accompanying drawings described herein are used for providing further understanding of the present invention, as a constitute part of the present invention. The illustrative examples of the present invention and the description thereof serve to explain the present invention, instead of limiting same improperly.

FIG. 1 shows a Brillouin scattering imaging-optical coherence elastography-laser speckle elastography based multi-mode elasticity measurement imaging device according to the present invention.

REFERENCE NUMERALS

1—narrow linewidth continuous laser 2—first optical fiber isolator 3—optical fiber delay line 4—optical fiber circulator 5—first collimator 6—beam splitter 7—ultra-wideband light emitting diode 8—second optical fiber isolator 9—2*2 optical fiber coupler 10—second collimator 11—dichroic mirror 12—galvanometer set 13—first optical shutter 14—objective lens 15—third collimator 16—attenuator 17—first plane reflector 18—fourth collimator 19—grating spectrometer 20—plano-convex lens 21—linear array charge coupled device (CCD) 22—fifth collimator 23—Brillouin spectrometer 24—first detector 25—second optical shutter 26—second plane reflector 27—beam expander 28—turnover reflector 29—second detector 30—sample and 31—time sequence controller 32—computer 33—signal generator 34—power amplifier and 35—ultrasonic transducer.

DETAILED DESCRIPTION

The section will describe the particular examples of the present invention in detail, and the preferred examples of the present invention are shown in the accompanying drawings. The accompanying drawings are used to supplement the description of the text portion of the description with FIGURES, so that people can intuitively and vividly understand each technical feature and the overall technical solution of the present invention, but should not be interpreted as limiting the scope of protection of the present invention.

In the description of the present invention, several means one or more, a plurality of means two or more, greater than, less than, over, etc. are interpreted as excluding the recited number, and above, below, within, etc. are interpreted as including the recited number. The description of first and second, if any, is only for distinguishing between technical features, and should not be interpreted as indicating or implying relative importance or implicitly indicating the number or the sequential relation of technical features indicated.

With reference to FIG. 1, in the preferred example of the present invention, a Brillouin-optical coherence-speckle based multi-mode elasticity measurement device includes a Brillouin-optical coherence elastography common-path scanning unit, a Brillouin scattering elastography system, an optical coherence elastography system, a speckle elastography system, and a time sequence controller 31, where the Brillouin scattering elastography system and the optical coherence elastography system share the Brillouin-optical coherence elastography common-path scanning unit, and the Brillouin-optical coherence elastography common-path scanning unit is composed of a dichroic mirror 11, a scanning galvanometer 12, a first optical shutter 13, and an objective lens 14, and configured to obtain a Brillouin signal and an optical coherence signal of a sample 30 at the same time. Particularly, the Brillouin-optical coherence elastography common-path scanning unit realizes common-path propagation and excitation through the dichroic mirror 11, so that the Brillouin scattering elastography system and the optical coherence elastography system realize in-situ synchronous measurement; where the Brillouin scattering elastography system includes a Brillouin signal excitation unit and a Brillouin signal acquisition unit, the Brillouin signal excitation unit being configured to excite a Brillouin scattering signal, and the Brillouin signal acquisition unit being configured to acquire a Brillouin spectrum signal, so as to calculate a bulk elasticity modulus; the optical coherence elastography system includes an optical coherence tomography unit and an acoustic radiation force excitation unit, the optical coherence tomography unit being configured to collect an interference signal generated in the sample 30, and the acoustic radiation force excitation unit being configured to generate vibration for the sample 30, so as to generate wave propagation; the speckle elastography system includes a speckle signal excitation unit and a speckle signal acquisition unit, the speckle signal excitation unit being configured to excite a wide-view field speckle signal generated on a surface of the sample 30, and the speckle signal acquisition unit being configured to collect the wide-view field speckle signal generated on the surface of the sample 30, so as to generate elasticity information; and the time sequence controller 31 is principally configured for step running of the Brillouin scattering elastography system, the optical coherence elastography system, and the speckle elastography system.

As the preferred embodiment of the present invention, the device may further have the additional technical features as follows:

In the present example, the Brillouin scattering signal excitation unit is composed of a narrow linewidth continuous laser 1, a first optical fiber isolator 2, an optical fiber delay line 3, an optical fiber circulator 4, a first collimator 5, and a beam splitter 6; the Brillouin signal acquisition unit is composed of a fifth collimator 22, a Brillouin spectrometer 23, and a first detector 24; and in the Brillouin elastography system, the narrow linewidth continuous laser 1 emits a light beam, the light beam passes through the first optical fiber isolator 2, the optical fiber delay line 3, port 1 of the optical fiber circulator 4, port 2 of the optical fiber circulator 4, and the first collimator 5, and is then split by the beam splitter 6, a reflected light passes through the dichroic mirror 11, a galvanometer set 12, and the first optical shutter 13, and is then focused on a surface of the sample 30 by the objective lens 14 to interact with the sample 30 to generate backward Brillouin scattering, and a backward Brillouin scattered light of the sample 30 returns along an original path, and is output from port 3 of the optical fiber circulator 4, and collimated by the fifth collimator 22 to enter the Brillouin spectrometer 23 for frequency discrimination, and is finally received by the first detector 24.

In the present example, light beams emitted by the Brillouin scattering elastography system, the optical coherence elastography system, and the speckle elastography system reach the sample 30 at the same time for measurement through the time sequence controller 31 and the optical fiber delay line 3, so that in-situ synchronous measurement on elasticity of the sample 30 in a wide-view field, high-speed, and high-precision manner is realized.

In the present example, the optical coherence tomography unit is composed of an ultra-wideband light emitting diode 7, a second optical fiber isolator 8, a 2*2 optical fiber coupler 9, a second collimator 10, a reference arm, a grating spectrometer 19, and a linear array charge coupled device (CCD) 21; the acoustic radiation force excitation unit is composed of a signal generator 33, a power amplifier 34, and an ultrasonic transducer 35; in the optical coherence elastography system, the ultra-wideband light emitting diode 7 emits a light beam, the light beam is collimated by the second optical fiber isolator 8, the 2*2 optical fiber coupler 9, and the second collimator 10, and then reflected by the dichroic mirror 11, a reflected light passes through the galvanometer set 12 and the first optical shutter 13, and is then focused on the sample 30 to be detected by the objective lens 14, a backscattered light generated through an interaction with the sample 30 returns along an original path, interferes with a light beam returned by the reference arm in the 2*2 optical fiber coupler 9, enters the grating spectrometer 19, and is acquired and received by the linear array CCD 21; and moreover, a trigger signal generated by the optical coherence elastography system is synchronized with the signal generator 33 to generate a sine wave signal which is amplified by the power amplifier 34 to excite the sample through the ultrasonic transducer 35, so that the sample 30 vibrates, and is acquired by the optical coherence tomography unit in the optical coherence elastography system.

Particularly, the reference arm includes a third collimator 15, an attenuator 16, and a first plane reflector 17, and the grating spectrometer 19 includes a fourth collimator 18, a grating, and a plano-convex lens 20.

In the present example, the ultrasonic transducer 35 includes an ultrasonic generation unit and an impedance matching couplant, the impedance matching couplant being principally attached to the ultrasonic generation unit for matching a third medium so as to reduce attenuation of acoustic radiation power in the case of propagation in air.

In the present example, the speckle signal excitation unit is composed of a narrow linewidth continuous laser 1, a first optical fiber isolator 2, an optical fiber delay line 3, an optical fiber circulator 4, a first collimator 5, a beam splitter 6, a second optical shutter 25, a second plane reflector 26, and a beam expander 27; the speckle signal acquisition unit is composed of an objective lens 14, a turnover reflector 28, and a second detector 29; and in a speckle detection system, the narrow linewidth continuous laser 1 emits a light beam, the light beam passes through the first optical fiber isolator 2, the optical fiber delay line 3, port 1 of the optical fiber circulator 4, port 2 of the optical fiber circulator 4, and the first collimator 5, and is then split by the beam splitter 6, a light beam transmitted through the beam splitter 6 passes through the second optical shutter 25, the second plane reflector 26, and the beam expander 27, and is then incident on the sample 30 to be detected, a scattered signal generated through an interaction with the sample 30 to be detected is reflected by the turnover reflector 28 to the second detector 29 through the objective lens 14 for detection.

Particularly, the speckle signal reception unit reflects the speckle signal through the turnover reflector 28 so as to acquire the signal when the speckle detection system detects the sample 30. When the speckle detection system does not work, a detection light of the Brillouin-optical coherence elastography common-path scanning unit is transmitted through the turnover reflector 28 as well.

In the present example, the speckle signal excitation unit and the Brillouin-optical coherence elastography common-path scanning unit are alternately used by alternately using the first optical shutter 13, the second optical shutter 25, and the turnover reflector 28.

In the present example, the Brillouin-optical coherence elastography common-path scanning unit scans a surface X-Y of the sample 30 through the galvanometer set 12 to obtain a three-dimensional elasticity distribution of optical coherence elastography (OCE), and the sample 30 at different depths by adjusting a focal length of the objective lens 14 to obtain a three-dimensional Brillouin elasticity distribution image.

Particularly, measurement on biological tissue is principally divided into eight steps:

Step 1, an optical coherence tomography system is turned on; and the optical coherence elastography system without the acoustic radiation force excitation unit may be regarded as the optical coherence tomography system approximately to detect a tissue structure. The second optical shutter 25 is closed to block the light beam from entering the speckle signal excitation unit, the first optical shutter 13 is opened, and the turnover reflector 28 is rotated away from the optical path, so that the light beam behind the galvanometer set 12 may pass through the first optical shutter 13, and then enter the objective lens 14.

Step 2, the optical coherence tomography system detects the tissue structure. Particularly, in the optical coherence tomography unit of the optical coherence elastography system, a 850-nm excitation light released by the ultra-wideband light emitting diode 7 passes through the second optical fiber isolator 8 and the 2*2 optical fiber coupler 9, is then collimated by the second collimator 10, and enters the Brillouin-optical coherence elastography common-path scanning unit. A backscattered signal returning along the original path is reflected by the dichroic mirror 11, passes through the second collimator 10, enters the 2*2 optical fiber coupler 9, and is output by the fourth collimator 18. An output scattered signal is split by the grating spectrometer 19, and then focused into the linear array CCD 21 by the plano-convex lens 20 to acquire the signal. The acquired signal is processed through a computer 32 to obtain structure information of biological tissue.

Step 3, the system is switched, and the speckle detection system is turned on. The second optical shutter 25 is opened, the light beam enters the speckle signal excitation unit, the first optical shutter 13 is closed, and the turnover reflector 28 enables the light beam to be incident into an acquisition optical path of the speckle elastography system.

Step 4, the acoustic radiation force excitation unit is turned on to generate a low-frequency ultrasonic signal, and an acoustic radiation force system applies an external acting force to the sample 30, so that an elastic wave is propagated in the sample 30. Details are as follows:

① The time sequence controller 31 generates an external trigger signal to the signal generator 33 through a connection line to generate a sine wave modulation signal. The sine wave modulation signal is amplified by the power amplifier 34 to drive the ultrasonic transducer 35 to generate an excitation force.

② The impedance matching couplant in the ultrasonic transducer 35 is principally attached to the ultrasonic generation unit for matching a third medium to reduce attenuation of acoustic radiation power in the case of propagation in air.

Step 5, the speckle elastography system performs wide-field elastography on the sample 30 to detect a propagation process of the elastic wave in the tissue within a wide view field. Details are as follows:

① When the speckle elastography system performs wide-field scanning, the second optical shutter 25 is opened, and the speckle signal excitation unit is turned on; and the turnover reflector 28 is rotated into the optical path, and the speckle signal reception unit is turned on.

② In the speckle signal excitation unit, after passing through the second optical shutter 25, a light beam split by the beam splitter 6 is reflected by the second plane reflector 26, then incident into the beam expander 27 for beam expansion, and finally hit on the sample 30 in a form of a wide-field light spot to interact with the sample 30.

③ In the speckle signal reception unit, the speckle signal generated at the sample 30 is reflected by the turnover reflector 28 through the objective lens 14 to enter the detector 29, so as to acquire the speckle signal, and the acquired signal is processed through a computer 32.

Step 6, the system is switched; and the speckle detection system is closed, and the Brillouin scattering elastography system and the optical coherence elastography system are turned on. The second optical shutter 25 is closed to block the light beam from entering the speckle signal excitation unit. The first optical shutter 13 is opened, and the turnover reflector 28 is rotated away from the optical path, so that the light beam behind the galvanometer set 12 may pass through the first optical shutter 13, and is then incident into the objective lens 14.

Step 7, the acoustic radiation force excitation unit is turned on to generate a high-frequency ultrasonic signal, and applies an external acting force to the sample 30, so that an elastic wave is propagated in the sample 30.

Step 8, when the Brillouin scattering elastography system and the optical coherence elastography system measure an elasticity modulus of the sample 30 at the same time, the Brillouin scattering elastography system obtains a bulk elasticity modulus of the tissue in a high-precision manner, the optical coherence elastography system obtains an elasticity distribution image of the tissue rapidly in a high-speed and high-sensitivity manner. The Brillouin scattering elastography system and the optical coherence elastography system share a Brillouin-optical coherence elastography scanning unit. Therefore, in-situ synchronous measurement of the Brillouin elastography system and the optical coherence elastography system may be realized. Details are as follows:

① The shared Brillouin-optical coherence elastography scanning unit principally includes the dichroic mirror 11, the galvanometer set 12, the first optical shutter 13, and the objective lens 14, where the dichroic mirror 11 transmits the excitation light of the Brillouin scattering elastography system to enter the Brillouin-optical coherence elastography common-path scanning unit, and reflects the excitation light of the optical coherence elastography system to enter the Brillouin-optical coherence elastography common-path scanning unit, and the light beams entering the Brillouin-optical coherence elastography common-path scanning unit are finally focused on the sample 30 to interact with the sample 30, so as to generate the scattered signal.

②In the Brillouin scattering signal excitation unit, a 780-nm excitation light released by the narrow linewidth continuous laser 1 passes through the first optical fiber isolator 2 and the optical fiber delay line 3, and then enters port 1 of the circulator 4. A spatial light output from port 2 of the circulator 4 is collimated by the first collimator 5, and split by the beam splitter 6, and part of the light enters the Brillouin-optical coherence elastography common-path scanning unit.

③In the optical coherence tomography unit in the optical coherence elastography system, a 850-nm excitation light released by the ultra-wideband light emitting diode 7 passes through the second optical fiber isolator 8 and the 2*2 optical fiber coupler 9, and is then collimated by the second collimator 10 to enter the Brillouin-optical coherence elastography common-path scanning unit.

④The time sequence controller 31 and the optical fiber delay line 3 are adjusted to control a time sequence of the narrow linewidth continuous laser 1 and ultra-wideband light emitting diode 7 to ensure that light beams output by the narrow linewidth continuous laser 1 and the ultra-wideband light emitting diode 7 reach the dichroic mirror 11 at the same time.

⑤A signal light generated at the sample 30 returns from the Brillouin-optical coherence elastography common-path scanning unit along the original optical path, and is acquired by the signal reception unit. The Brillouin scattering elastography system and the optical coherence elastography system have independent signal reception units. In the Brillouin scattering signal reception unit, a backward Brillouin scattered signal generated at the sample 30 returns along the original optical path, passes through the optical fiber circulator 4, is then collimated by the fifth collimator 22, enters the Brillouin spectrometer 23, and undergoes spectral detection by the first detector 24, and an acquired spectral signal is processed through the computer 32.

⑥In an acquisition unit of the optical coherence elastography system, the backward scattered signal returning along the original path of the Brillouin-optical coherence elastography common-path scanning unit is reflected by the dichroic mirror 11, passes through the second collimator 10 to enter the 2*2 optical fiber coupler 9, and is output by the fourth collimator 18. An output scattered signal is split by the grating spectrometer 19, focused into the linear array CCD 21 by the plano-convex lens 20 to acquire the signal, and the collected signal is processed through the computer 32.

A person skilled in the art can combine and superimpose the additional technical features described above at random without conflict.

What are described above are only the preferred embodiments of the present invention, and the technical solutions that realize the objective of the present invention through basically the same means fall within the scope of protection of the present invention.

What is claimed is:

1. A Brillouin-optical coherence-speckle based multimode elasticity measurement device, comprising: a Brillouin-optical coherence elastography common-path scanning unit, a Brillouin scattering elastography system, an optical coherence elastography system, a speckle elastography system, and a time sequence controller, wherein the Brillouin scattering elastography system and the optical coherence elastography system share the Brillouin-optical coherence elastography common-path scanning unit, and the Brillouin-optical coherence elastography common-path scanning unit is composed of a dichroic mirror, a scanning galvanometer, a first optical shutter, and an objective lens; wherein the Brillouin scattering elastography system comprises a Brillouin signal excitation unit and a Brillouin signal acquisition unit, the Brillouin signal excitation unit being configured to excite a Brillouin scattering signal, and the Brillouin signal acquisition unit being configured to acquire a Brillouin spectrum signal, so as to calculate a bulk elasticity modulus; the optical coherence elastography system comprises an optical coherence tomography unit and an acoustic radiation force excitation unit, the optical coherence tomography unit being configured to collect an interference signal generated in a sample, and the acoustic radiation force excitation unit being configured to generate vibration for the sample, so as to generate wave propagation; the speckle elastography system comprises a speckle signal excitation unit and a speckle signal acquisition unit, the speckle signal excitation unit being configured to excite a wide-view field speckle signal generated on a surface of the sample, and the speckle signal acquisition unit being configured to collect the wide-view field speckle signal generated on the surface of the sample, so as to generate elasticity information; and the time sequence controller is principally configured for step running of the Brillouin scattering elastography system, the optical coherence elastography system, and the speckle elastography system.

2. The Brillouin-optical coherence-speckle based multimode elasticity measurement device according to claim 1, wherein the Brillouin scattering signal excitation unit is composed of a narrow linewidth continuous laser, a first optical fiber isolator, an optical fiber delay line, an optical fiber circulator, a first collimator, and a beam splitter; the Brillouin signal acquisition unit is composed of a fifth collimator, a Brillouin spectrometer, and a first detector; and in the Brillouin elastography system, the narrow linewidth continuous laser emits a light beam, the light beam passes through the first optical fiber isolator, the optical fiber delay line, port 1 of the optical fiber circulator, port 2 of the optical fiber circulator, and the first collimator, and is then split by the beam splitter, a reflected light passes through the dichroic mirror, a galvanometer set, and the first optical shutter, is then focused on a surface of the sample by the objective lens, and interacts with the sample to generate backward Brillouin scattering, a backward Brillouin scattered light of the sample returns along an original optical path, is output from port 3 of the optical fiber circulator, and collimated by the fifth collimator, enters the Brillouin spectrometer for frequency discrimination, and is finally received by the first detector.

3. The Brillouin-optical coherence-speckle based multimode elasticity measurement device according to claim 1, wherein the Brillouin scattering elastography system, the optical coherence elastography system, and the speckle elastography system are integrated, and light beams emitted by the laser reach the sample at the same time for measurement through the time sequence controller and the optical fiber delay line, so that in-situ synchronous measurement on elasticity of the sample in a wide-view field, high-speed, and high-precision manner is realized.

4. The Brillouin-optical coherence-speckle based multimode elasticity measurement device according to claim 1, wherein the optical coherence tomography unit is composed of an ultra-wideband light emitting diode, a second optical fiber isolator, a 2*2 optical fiber coupler, a second collimator, a reference arm, a grating spectrometer, and a linear array charge coupled device (CCD) 21; the acoustic radiation force excitation unit is composed of a signal generator, a power amplifier, and an ultrasonic transducer; in the optical coherence elastography system, the ultra-wideband light emitting diode emits a light beam, the light beam is collimated by the second optical fiber isolator, the 2*2 optical fiber coupler, and the second collimator, and then reflected by the dichroic mirror, a reflected light passes through a galvanometer set and the first optical shutter, and is then focused on the sample to be detected by the objective lens, a backscattered light generated through an interaction with the sample returns along an original path, interferes with a light beam returned by the reference arm in the 2*2 optical fiber coupler, enters the grating spectrometer, and is acquired and received by the linear array CCD; and moreover, a trigger signal generated by the optical coherence elastography system is synchronized with the signal generator to generate a sine wave signal which is amplified by the power amplifier to excite the sample through the ultrasonic transducer, so that the sample vibrates, and is acquired by the optical coherence tomography unit in the optical coherence elastography system.

5. The Brillouin-optical coherence-speckle based multimode elasticity measurement device according to claim 4, wherein the ultrasonic transducer comprises an ultrasonic generation unit and an impedance matching couplant, the impedance matching couplant being principally attached to the ultrasonic generation unit for matching a third medium so as to reduce attenuation of acoustic radiation power in the case of propagation in air.

6. The Brillouin-optical coherence-speckle based multimode elasticity measurement device according to claim 1, wherein the speckle signal excitation unit is composed of a narrow linewidth continuous laser, a first optical fiber isolator, an optical fiber delay line, an optical fiber circulator, a first collimator, a beam splitter, a second optical shutter, a second plane reflector, and a beam expander; the speckle signal acquisition unit is composed of an objective lens, a turnover reflector, and a second detector; and in a speckle detection system, the narrow linewidth continuous laser emits a light beam, the light beam passes through the first optical fiber isolator, the optical fiber delay line, port 1 of the optical fiber circulator, port 2 of the optical fiber circulator, and the first collimator, and is then split by the beam splitter, a light beam transmitted through the beam splitter passes through the second optical shutter, the second plane reflector, and the beam expander, and is then incident on the sample to be detected, and a scattered signal generated through an interaction with the sample to be detected is reflected by the turnover reflector into the second detector through the objective lens for detection.

7. The Brillouin-optical coherence-speckle based multimode elasticity measurement device according to claim 6, wherein the speckle signal excitation unit and the Brillouin-optical coherence elastography common-path scanning unit are alternately used by alternately using the first optical shutter, the second optical shutter, and the turnover reflector.

8. The Brillouin-optical coherence-speckle based multimode elasticity measurement device according to claim 1, wherein the Brillouin-optical coherence elastography common-path scanning unit scans a surface X-Y of a sample through a galvanometer set to obtain a three-dimensional elasticity distribution of optical coherence elastography (OCE), and the sample at different depths by adjusting a focal length of the objective lens to obtain a three-dimensional Brillouin elasticity distribution image.

* * * * *